US00PP09625P

United States Patent [19]

Van Der Voort

[11] Patent Number: Plant 9,625

[45] Date of Patent: Aug. 13, 1996

[54] LILY PLANT NAMED 'NIPPON'

[75] Inventor: Cees A. Van Der Voort, Katwijk, Netherlands

[73] Assignee: Vletter & Den Haan Beheer B.V., Rijnsburg, Netherlands

[21] Appl. No.: 440,661

[22] Filed: May 15, 1995

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A lily plant named Nippon particularly characterized by its brown pollen color that contrasts nicely with the white ground color of the tepals, yellow stripes on the midveins of the tepals and spots on the lower half of the tepals.

1 Drawing Sheet

The present invention comprises a new and distinct cultivar of lily, botanically known as Lilium Oriental Hybrid and hereinafter referred to by the cultivar name Nippon.

The new cultivar is a product of a planned breeding program which had the objectives of creating a new white oriental lily cultivar with good forcing habits.

The new cultivar was originated from a hybridization made by the inventor in a controlled breeding program in Rijnsburg, The Netherlands in June 1983. The male and female parents were unnamed and proprietary seedlings.

Nippon was discovered and selected as one flowering plant within the progeny of the stated cross by the inventors in July 1986 in a controlled environment in Rijnsburg, The Netherlands.

The first act of asexual reproduction of the new cultivar was accomplished by the inventor when scales were taken in 1987 from the initial selection in a controlled environment in Rijnsburg, The Netherlands. Horticultural examination of selected units has demonstrated that the combination of characteristics as herein disclosed for the Nippon are firmly fixed and are retained through successive generations of asexual reproduction.

Nippon has not been observed under all possible environmental conditions. The phenotype may vary significantly with variations in environment such as temperature, light intensity, and daylength, without, however, any variance in genotype.

The following observations, measurements and comparisons describe plants grown in Wageningen, The Netherlands under greenhouse conditions which approximate those generally used in commercial practice.

The following traits have been repeatedly observed and are determined to be basic characteristics of Nippon which in combination distinguish this lily as a new and distinct cultivar.

1. The color of the pollen is brown and contrasts nicely with the ground color of the tepals.

2. The tepals have an intense yellow stripe on the midvein.

3. Spots are present on lower half of tepals.

Of the many commercial cultivars known to the inventors, the most similar in comparison to the new cultivar is Arena (Identification/Breeders Ref. 86-177). In comparison to Arena, Nippon has brown instead of orange pollen, a bright yellow mid-vein instead of yellow-red, and larger stems.

The accompanying photographic drawing shows typical flower characteristics of the new cultivar, with colors being as true as possible with illustrations of this type.

In the following description, color references are made to The Royal Horticultural Society (R.H.S.) Colour Chart. The color values were determined at Wageningen, The Netherlands in June 1994.

Origin: Seedling from breeding program.

Parentage:

*Seed parent.*—Unnamed seedling.

*Pollen parent.*—Unnamed seedling.

Classification:

*Botanical.*—Lilium cv. Nippon.

*Commercial.*—Oriental Hybrid.

Plant:

*Form.*—A single stem carrying numerous pedicels alternately arranged.

*Height.*—On opening of anthers of first flower medium to high.

*Growth habit.*—Vigorous.

*Stem.*—Circular in transverse section; antocyanin pigmentation present in spots and stripes.

*Foliage.*—Quantity: From small to medium leaves, depending on growing conditions. Size of leaf: Mature leaves are approximately 3 cm wide and 15 cm long. Shape of leaves: Elliptical. Color: R.H.S. 137B.

*Bulbs.*—Size: 16–18 cm in circumference. Color: White.

Bud:

*Form.*—Tapering like a lancet.

*Size.*—13 cm in length depending on growing conditions.

*Opening.*—Unfolds normally.

*Color.*—R.H.S. 145D.

*Tepals.*—Folded and three visible.

Flower:

*Blooming habit.*—Raceme.

*Size.*—22 cm in diameter depending on growing conditions.

*Borne.*—Upright to horizontal.

*Shape.*—Generally hexagonal star in form and bowl-shaped in cross-section.

*Tepalage.*—Number of Tepals: Six. Arrangement: Three inner and three outer. Color (upper surface): White R.H.S. 155D; senescence initiates a purple shade. Color (lower surface): White R.H.S. 155D; senescence initiates a purple shade. Spotting or marking: Spots are present on the lower half of tepal (R.H.S. 67C). There is a yellow stripe along the midvein.

*Pedicel.*—Length: 10 cm (first flower) depending on growing condition. Color: Medium green with anthocyanin pigmentation. Form: Slightly curved.

*Texture.*—Papillose.

*Disease resistance.*—No disease problems noted to date.

*Fragrance.*—Present (weak).

*Lasting quality.*—Excellent.

Reproductive organs:

*Stamens and anthers.*—Arrangements: Anthers form a generally circular pattern at their upper ends. Length: 8 cm. Number: Six. Filaments: Green.

*Pollen color.*—Brown.

*Anther color.*—R.H.S. 175C.

*Pistils.*—Green (R.H.S. 145D).

*Stigma.*—Gray (R.H.S. 202D).

*Ovaries.*—Triangular in shape.

It is claimed:

1. A new and distinct lily plant named Nippon, as described and illustrated.

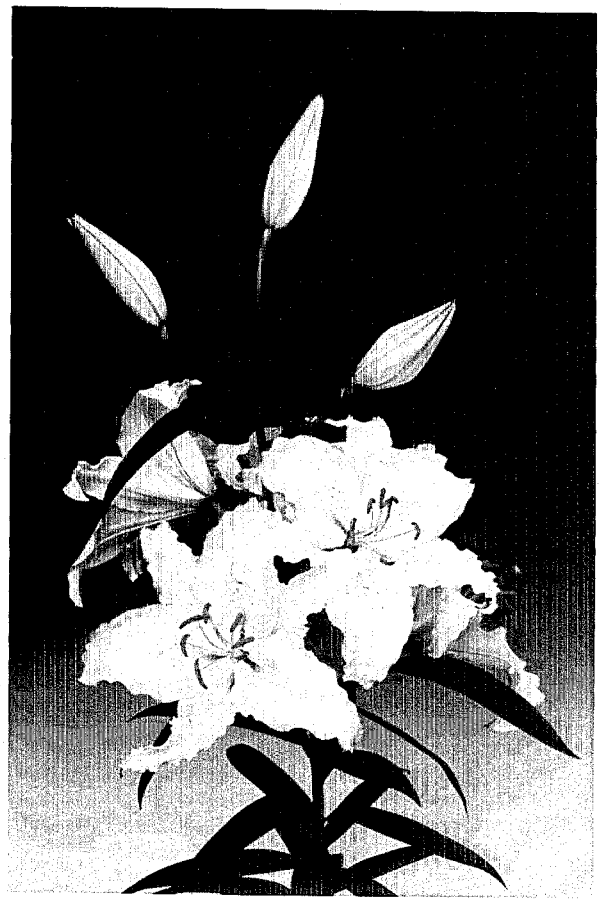

* * * * *